(12) United States Patent
Hinayama et al.

(10) Patent No.: US 9,982,069 B2
(45) Date of Patent: May 29, 2018

(54) WATER-ABSORBENT RESIN AND ABSORBENT ARTICLE

(71) Applicant: Sumitomo Seika Chemicals Co. Ltd., Kako-gun, Hyogo (JP)

(72) Inventors: Tetsuhiro Hinayama, Himeji (JP); Masahiro Murakami, Himeji (JP); Hiroki Yabuguchi, Himeji (JP); Hideki Yokoyama, Himeji (JP)

(73) Assignee: Sumitomo Seika Chemicals Co., Ltd., Hyogo (JP)

( * ) Notice: Subject to any disclaimer, the term of this patent is extended or adjusted under 35 U.S.C. 154(b) by 0 days. days.

(21) Appl. No.: 14/784,259

(22) PCT Filed: Nov. 4, 2014

(86) PCT No.: PCT/JP2014/079244
§ 371 (c)(1),
(2) Date: Oct. 13, 2015

(87) PCT Pub. No.: WO2016/006131
PCT Pub. Date: Jan. 14, 2016

(65) Prior Publication Data
US 2017/0107312 A1    Apr. 20, 2017

(30) Foreign Application Priority Data

Jul. 11, 2014 (JP) ................... 2014-143716
Oct. 31, 2014 (JP) ................... 2014-223723

(51) Int. Cl.
| | |
|---|---|
| *C08F 220/06* | (2006.01) |
| *C08J 3/24* | (2006.01) |
| *C08F 120/06* | (2006.01) |
| *A61F 13/53* | (2006.01) |
| *A61L 15/24* | (2006.01) |
| *A61L 15/60* | (2006.01) |

(52) U.S. Cl.
CPC ............ *C08F 120/06* (2013.01); *A61F 13/53* (2013.01); *A61L 15/24* (2013.01); *A61L 15/60* (2013.01); *C08J 3/24* (2013.01); *C08F 220/06* (2013.01); *C08F 2810/20* (2013.01); *C08J 2333/02* (2013.01)

(58) Field of Classification Search
CPC ...... C08F 220/06; C08F 20/06; C08F 120/06; C08J 3/24; C08J 3/243; C08J 3/245; C08J 2333/02
See application file for complete search history.

(56) References Cited

U.S. PATENT DOCUMENTS

| | | | |
|---|---|---|---|
| 5,985,944 A | 11/1999 | Ishizaki et al. | |
| 6,906,159 B2 | 6/2005 | Dairoku et al. | |
| 8,003,210 B2 | 8/2011 | Kobushi et al. | |
| 8,742,023 B2 | 6/2014 | Fujimura et al. | |
| 2002/0040095 A1 | 4/2002 | Dairoku et al. | |
| 2004/0110006 A1 | 6/2004 | Ishizaki et al. | |
| 2004/0110913 A1 | 6/2004 | Kanto et al. | |
| 2004/0110914 A1 | 6/2004 | Nakahara et al. | |
| 2006/0252913 A1* | 11/2006 | Herfert ................... | A61L 15/60 528/480 |
| 2008/0280154 A1* | 11/2008 | Kobushi ................. | A61L 15/60 428/500 |
| 2009/0239071 A1* | 9/2009 | Stueven .................. | A61L 15/60 428/402 |
| 2010/0062932 A1 | 3/2010 | Losch et al. | |
| 2011/0301560 A1 | 12/2011 | Fujimura et al. | |
| 2013/0273351 A1 | 10/2013 | Takatori et al. | |
| 2016/0280825 A1* | 9/2016 | Bauer .................... | C08F 220/06 |

FOREIGN PATENT DOCUMENTS

| | | |
|---|---|---|
| EP | 0780424 A1 | 6/1997 |
| EP | 1882701 A1 | 1/2008 |
| EP | 2700663 A1 | 2/2014 |
| EP | 2993189 A1 | 3/2016 |
| EP | 2993191 A1 | 3/2016 |
| EP | 2998325 A1 | 3/2016 |
| JP | 9-136966 | 5/1997 |
| JP | 11-335404 | 7/1999 |
| JP | 11-347402 | 12/1999 |
| JP | 2000-026510 A | 1/2000 |

(Continued)

OTHER PUBLICATIONS

"Certified Experimental Results" Plaintiff's Exhibit No. 2, Nippon Shokubai Co. Ltd., Nov. 10, 2015.*
Database WPI Week 201213 Thomson Scientific, London, GB; AN 2012-003537 XP002764086.
Database EPODOC [Online] European Patent Office, The Hague, NL; XP002764087.
Database WPI Week 200009 Thomson Scientific, London, GB; AN 2000-101036 XP002764088.

(Continued)

*Primary Examiner* — Robert Rabago
(74) *Attorney, Agent, or Firm* — Locke Lord LLP

(57) ABSTRACT

The following are provided: a water-absorbent resin in which, in the formation of an absorbent material forming an absorbent article, dispersion is satisfactory even in a moisture absorption state, which prevents the occurrence of troubles at the time of manufacturing of the absorbent article and which allows efficient manufacturing; and an absorbent article using an absorbent material containing the water-absorbent resin. The water-absorbent resin according to the present invention is obtained by polymerizing a water-soluble ethylenically unsaturated monomer and performing post-crosslinking thereon with a post-crosslinking agent, and the water-absorbent resin satisfies the requirements below:

(A) yellow index is 5.0 or less; and
(B) gel strength is 1800 Pa or less.

3 Claims, 1 Drawing Sheet

(56) References Cited

FOREIGN PATENT DOCUMENTS

| JP | 2002-212204 A | 7/2002 |
|----|---------------|--------|
| JP | 2003-246810 A | 9/2003 |
| JP | 2003-246812 A | 9/2003 |
| JP | 2006-522181 A | 9/2006 |
| JP | 2008-535640 A | 9/2008 |
| JP | 2010-518208 A | 5/2010 |
| JP | 2012-012482 A | 1/2012 |
| JP | 2012-031292 A | 2/2012 |
| JP | 2012-236898 A | 12/2012 |
| JP | 2013-231199 A | 11/2013 |
| WO | WO-96/17884 A1 | 6/1996 |
| WO | WO-2004/085496 A1 | 10/2004 |
| WO | WO-2006/109882 A1 | 10/2006 |
| WO | WO-2006/123561 A1 | 11/2006 |
| WO | WO-2012081355 A1 | 6/2012 |

OTHER PUBLICATIONS

Database EPODOC [Online] European Patent Office, The Hague, NL; XP002764089.
Frederic L Buchholz et al. (editors), "Modern Superabsorbent Polymer Technology" In: "Modern Superabsorbent Polymer Technology," vol. 3, Jan. 1, 1997, XP055319182 (22 pages).
Supplementary European Search Report dated Nov. 30, 2016, issued for European Patent Application No. 14882126.7.
"Certified Experimental Results" Plaintiff's Exhibit No. 2, Nippon Shokubai Co Ltd, Nov. 10, 2015 and English translation thereof (6 pages).
International Search Report for PCT/P2014/079244 dated Dec. 2, 2014.

* cited by examiner

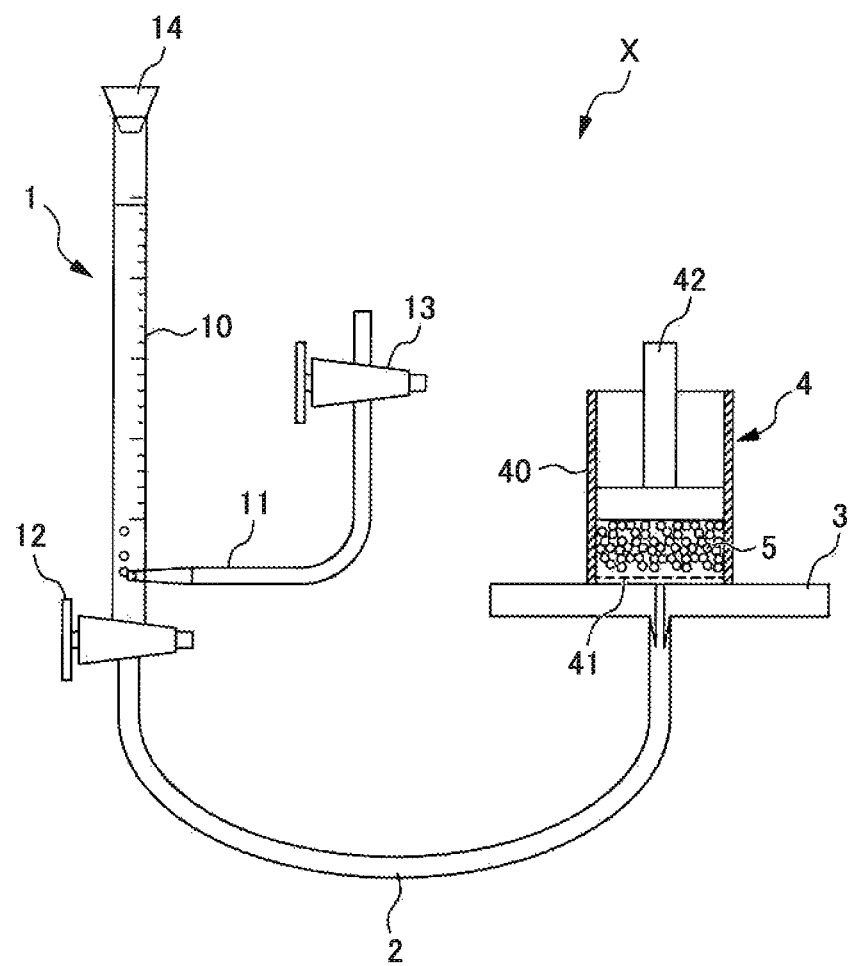

WATER-ABSORBENT RESIN AND ABSORBENT ARTICLE

CROSS-REFERENCE TO RELATED APPLICATIONS

This application is the national phase under 35 U.S.C. § 371 of PCT International Application No. PCT/JP2014/079244, filed Nov. 4, 2014, which claims the benefit of Japanese Application No. 2014-143716, filed Jul. 11, 2014, and Japanese Application No. 2014-223723, filed Oct. 31, 2014, the entire contents of the aforementioned applications are hereby incorporated herein by reference.

TECHNICAL FIELD

The present invention relates to a water-absorbent resin and an absorbent article, and more particularly relates to a water-absorbent resin forming an absorbent material suitably used for hygienic materials such as sanitary articles and disposable diapers and to an absorbent article using its resin.

BACKGROUND ART

In recent years, water-absorbent resins have been widely used in the fields of hygienic materials such as sanitary articles and disposable diapers.

For water-absorbent resins as described above, cross-linked products of partially neutralized polymers of acrylic acid are preferred because they have many advantages, including the followings: they have excellent water-absorption performance; their raw materials such as acrylic acid has easy industrial availability, and therefore they can be produced with stable quality and low cost; and they show no shortcomings such as in which decomposition is likely to occur.

In the fields of hygienic materials such as sanitary articles and disposable diapers, such a water-absorbent resin is used to form an absorbent material, and by the means that the absorbent material is held between a liquid permeable sheet (top sheet) through which a liquid can pass and a liquid impermeable sheet (back sheet) through which a liquid cannot permeate, it is possible to form an absorbent article.

An absorbent material formed with a water-absorbent resin is generally formed with the water-absorbent resin and a hydrophilic fiber. An absorbent material is formed as, for example, a mixed dispersion member obtained by mixing a water-absorbent resin and a hydrophilic fiber such that they have a uniform composition, a sandwich structure member in which a water-absorbent resin is sandwiched between layered hydrophilic fibers or a wrapped member in which a water-absorbent resin and an hydrophilic fiber is wrapped with tissue. Here, it is important to form an absorbent material in which a water-absorbent resin is uniformly dispersed in order to manufacture an absorbent article having an excellent quality.

In the manufacturing of the absorbent article having the absorbent material described above on an industrial scale, the water-absorbent resin may be exposed to the atmosphere for a long period of time such as by an unexpected stop of manufacturing facilities. Here, since the water-absorbent resin is hygroscopic, a part or the whole thereof may be aggregated. The water-absorbent resin aggregated as described above is significantly lowered in flowability, and thereby experiences troubles such as the occurrence of blocking within the piping of manufacturing facilities and the formation of a bridge within a powder hopper. Furthermore when the absorbent material described above is prepared, the aggregated water-absorbent resin may hinder its uniform dispersion.

In recent years, since an absorbent article and an absorbent material used for it tend to be decreased in thickness, there a tendency that the proportion of a bulky hydrophilic fiber and the like is reduced and to increase the proportion of the water-absorbent resin. Therefore, the properties of the water-absorbent resin suitable for the manufacturing facilities of the absorbent article tend to more significantly affect the ease of manufacturing of the absorbent material and the absorbent article using it.

In order to enhance the moisture absorption resistance of the water-absorbent resin described above, a technology is proposed in which surface treatment is performed on the particles of the water-absorbent resin with a surfactant such as a silicone-based surfactant or polyurethane having a specific functional group (see Patent Documents 1 and 2).

However, the water-absorbent resins obtained in these methods do not necessarily satisfy the problems described above, and there are still improvements to be made.

Moreover, conventional water-absorbent resins may be, depending on each resin individually, colored pale yellow or dark yellow in the state of a product. When as described above, the proportion of the water-absorbent resin is increased, and thus the absorbent material is decreased in thickness, if the water-absorbent resin is colored, the cleanliness of appearance of an absorbent article using that resin is lowered, with the result that the product value tends to be lowered.

PRIOR ART DOCUMENT

Patent Documents

Patent Document 1: Japanese Unexamined Patent Application, Publication No. H09-136966
Patent Document 2: Japanese Unexamined Patent Application, Publication No. H11-347402

DISCLOSURE OF THE INVENTION

Problems to be Solved by the Invention

The present invention is proposed in view of the foregoing situations, and has an object to provide a water-absorbent resin in which in the formation of an absorbent material forming an absorbent article, dispersion is satisfactory even in a moisture absorption state, which prevents the occurrence of troubles at the time of manufacturing of the absorbent article and which allows efficient manufacturing; and an absorbent article using an absorbent material containing the water-absorbent resin.

Means for Solving the Problems

The present inventors have performed thorough studies to solve the problems described above. Consequently, they have found that a water-absorbent resin in which the yellow index and the gel strength thereof are a predetermined value or less is excellent in flowability after moisture absorption. Specifically, the present invention provides the following.

(1) According to the present invention, there is provided a water-absorbent resin, were the water-absorbent resin is obtained by polymerizing a water-soluble ethylenically unsaturated monomer and performing post-crosslinking thereon with a post-crosslinking agent, and the water-absorbent resin satisfies requirements below:
(A) yellow index is 5.0 or less; and
(B) gel strength is 1800 Pa or less.
(2) In the water-absorbent resin of the invention according to the above item (1), a water-absorption capacity of physiological saline under a load of 4.14 kPa is 16 ml/g or more.
(3) According to the present invention, there is provided an absorbent article that uses an absorbent material containing the water-absorbent resin according to the above item (1) or (2).

Effects of the Invention

In the present invention, even in a moisture absorption state, the water-absorbent resin has satisfactory dispersion and can escape the occurrence of troubles at the time of manufacturing absorbent article such as blocking within piping and the formation of a bridge within a powder hopper. Therefore it is possible to efficiently manufacture an absorbent article.

BRIEF DESCRIPTION OF THE DRAWINGS

FIG. 1 A pattern diagram showing the schematic arrangement of a apparatus for measuring, in a water-absorbent resin, a water-absorption capacity of physiological saline under a load of 4.14 kPa.

PREFERRED MODE FOR CARRYING OUT THE INVENTION

The present invention will be described in detail below.
1. Water-Absorbent Resin
A water-absorbent resin according to the present invention has the following properties.
Specifically, the water-absorbent resin according to the present invention is a water-absorbent resin that is obtained by polymerizing a water-soluble ethylenically unsaturated monomer and performing post-crosslinking with a post-crosslinking agent, and satisfies the following properties:
(A) yellow index is 5.0 or less; and
(B) gel strength is 1800 Pa or less.
(A) Yellow Index
The water-absorbent resin according to the present invention is characterized in that its yellow index is 5.0 or less. The yellow index here refers to a value that is measured with a color-difference meter in which the tristimulus values X, Y and Z of a colorimetric color-difference meter are corrected with a standard white plate, and the yellow index (YI value) can be calculated by the formula below from the X, Y and Z of the water-absorbent resin that is a target to be measured. Moreover, the yellow index is preferably 0.0 or more.

yellow index=100(1.28$X$−1.06$Z$)/$Y$ (B) Gel Strength
The water-absorbent resin according to the present invention is characterized in that its gel strength is 1800 Pa or less. The gel strength here refers to a value that is measured with a method described later in examples and that is measured with a card meter (for example, a card meter made by I. Techno Engineering Co., Ltd., Product Number: ME-600) after 50 times swollen gel is stored in a constant temperature and humidity chamber for 15 hours. The gel strength is 1800 Pa or less, preferably 1600 Pa or less and more preferably 1500 Pa or less. Moreover, the gel strength is 500 Pa or more, preferably 600 Pa or more and further preferably 800 Pa or more.

The water-absorbent resin according to the present invention is excellent in flowability in a moisture absorption state. The flowability of the water-absorbent resin after the absorption of moisture can be evaluated by "a load of 4.14" described later in the examples.

In the water-absorbent resin of the present invention having the properties described above, when an absorbent article is manufactured therewith, even in a moisture absorption state, it is possible to reduce the aggregation of a part or the whole of the water-absorbent resin lot, and it is possible to reduce the occurrence of troubles at the time of manufacturing such as blocking within piping and the formation of a bridge within a powder hopper. It is also possible to form an absorbent material of satisfactory quality in which the water-absorbent resin is uniformly dispersed.

In the water-absorbent resin according to the present invention, its yellow index is low, and the cleanliness of an obtained absorbent material and an absorbent article containing the absorbent material is enhanced, with the result that it is possible to give a user a good impression and desire to purchase.

(C) Other Properties

In the water-absorbent resin according to the present invention, its median particle diameter is preferably 200 to 600 μm, more preferably 200 to 550 μm, further preferably 300 to 500 μm and further more preferably 300 to 450 μm.

In the water-absorbent resin according to the present invention, the mass proportion of particles from 150 to 850 μm is preferably 85 mass % or more, and more preferably 90 mass % or more. Furthermore, the mass proportion of particles from 300 to 400 μm is preferably 20 mass % or more, more preferably 25 mass % or more and further preferably 30 mass % or more.

The particles of the water-absorbent resin may be in the form in which each the particle is formed with a single particle or may be in the form (secondary particles) in which minute particles (primary particles) are agglomerated. Examples of the shape of the primary particle when the primary particle is manufactured by reverse phase suspension polymerization include a substantially spherical single-particle shape that has a smooth surface shape such as a spherical shape or a spheroidal shape. Since the surface shape is smooth in the primary particles with such a shape to increase the flowability of the powder thereof, and the agglomerated particles are easily and densely packed, the secondary particles are unlikely to be broken by a shock, and the water-absorbent resin having a high particle strength is obtained.

In the water-absorbent resin according to the present invention, its water-absorption capacity of physiological saline under a load of 4.14 kPa is preferably 16 ml/g or more, more preferably 18 ml/g or more and further preferably 20 ml/g or more. Moreover, the water-absorption capacity of physiological saline under a load is preferably 50 ml/g or less, and more preferably 40 ml/g or less.

In the water-absorbent resin described above, the yellow index, the gel strength, the water-absorption capacity of physiological saline under a load of 4.14 kPa, the median particle diameter (particle size distribution) and the flowability after the moisture absorption test can be evaluated with measurement methods described later in the examples respectively.

In order to provide various performances to the water-absorbent resin according to the present invention, it is possible to combine additives corresponding to purposes. Examples of such additives include an inorganic powder, a surfactant, an oxidizing agent, a reducing agent, a metal chelating agent, a radical chain inhibitor, an antioxidant, an antibacterial agent and a deodorant. For example, 0.05 to 5 mass parts of amorphous silica is added as an inorganic powder to 100 mass parts of the water-absorbent resin, and thus it is possible to enhance the flowability of the water-absorbent resin.

2. Method of Producing Water-Absorbent Resin

The water-absorbent resin according to the present invention can be produced by polymerizing a water-soluble ethylenically unsaturated monomer.

As the method of polymerizing the water-soluble ethylenically unsaturated monomer, a typical polymerization method such as an aqueous solution polymerization method, an emulsion polymerization method or a reverse phase suspension polymerization method is used. In the aqueous solution polymerization method, a water-soluble ethylenically unsaturated monomer aqueous solution is heated while being stirred as necessary, and thus the polymerization is performed. In the reverse phase suspension polymerization method, the water-soluble ethylenically unsaturated monomer is heated in a hydrocarbon dispersion medium under stirring, and thus the polymerization is performed. In the present invention, the reverse phase suspension polymerization method is preferable because it is possible to perform accurate polymerization reaction control and extensive particle diameter control.

An example of the method of producing the water-absorbent resin according to the present invention will be described below.

Specific examples of the method of producing the water-absorbent resin includes a method of producing the water-absorbent resin by performing the reverse phase suspension polymerization on the water-soluble ethylenically unsaturated monomer in a hydrocarbon dispersion medium that includes: a step of performing polymerization in the presence of an internal-crosslinking agent, at least in the presence of an azo based compound and a peroxide; and a step of performing, with a post-crosslinking agent, post-crosslinking on a hydrous gel-like material having an internal-crosslinking structure obtained by the polymerization.

Polymerization Step

[Water-Soluble Ethylenically Unsaturated Monomer]

Water-soluble ethylenically unsaturated monomers include, for example, (meth)acrylic acid ("(meth)acry" herein refers to both "acry" and "methacry". The same shall apply hereinafter) and salts thereof; 2-(meth)acrylamide-2-methylpropanesulfonic acid and salts thereof; nonionic monomers such as (meth)acrylamide, N,N-dimethyl(meth)acrylamide, 2-hydroxyethyl(meth)acrylate, N-methylol(meth)acrylamide, polyethylene glycol mono(meth)acrylate; amino group-containing unsaturated monomers such as N,N-diethylaminoethyl(meth)acrylate, N,N-diethylaminopropyl(meth)acrylate, diethylaminopropyl(meth)acrylamide and quaternary compounds thereof. Among these water-soluble ethylenically unsaturated monomers, (meth)acrylic acid or salts thereof, (meth)acrylamide, N,N-dimethylacrylamide are preferred in view of easy industrial availability, and (meth)acrylic acid and salts thereof are more preferred. Note that these water-soluble ethylenically unsaturated monomers may be used alone or in a combination of two or more.

Among these, acrylic acid and salts thereof are widely used as raw materials for water-absorbent resins, and may also be used in a case where the aforementioned water-soluble ethylenically unsaturated monomers are copolymerized with these partially neutralized polyacrylates. In this case, a partially neutralized polyacrylate is preferably used as a main water-soluble ethylenically unsaturated monomer in an amount of 70 to 100 mol % relative to the total amount of water-soluble ethylenically unsaturated monomers.

Preferably, a water-soluble ethylenically unsaturated monomer is dispersed in a hydrocarbon dispersion medium in the state of an aqueous solution, and subjected to reverse phase suspension polymerization. A water-soluble ethylenically unsaturated monomer in the form of an aqueous solution can increase the dispersion efficiency in a hydrocarbon dispersion medium. For the concentration of a water-soluble ethylenically unsaturated monomer in the aqueous solution, it is preferably in a range from 20 mass % to the saturation concentration or below. The concentration of the water-soluble ethylenically unsaturated monomer is more preferably 55 mass % or less, further preferably 50 mass % or less and further more preferably 45 mass % or less. On the other hand, the concentration of the water-soluble ethylenically unsaturated monomer is more preferably 25 mass % or more, and further preferably 28 mass % or more and further more preferably 30 mass % or more.

When a water-soluble ethylenically unsaturated monomer has an acid group such as (meth)acrylic acid, or 2-(meth)acrylamide-2-methylpropanesulfonic acid, those having the acid group pre-neutralized with an alkaline neutralizer may be used if desired. Such alkaline neutralizers include alkali metal salts such as sodium hydroxide, sodium carbonate, sodium hydrogen carbonate, potassium hydroxide, and potassium carbonate; and ammonia and the like. Further, these alkaline neutralizers may be used in the form of an aqueous solution in order to simply neutralization procedures. Note that the aforementioned alkaline neutralizers may be used alone or in a combination of two or more.

For the degree of neutralization of a water-soluble ethylenically unsaturated monomer with an alkaline neutralizer, the degree of neutralization of all acid groups in the water-soluble ethylenically unsaturated monomer is preferably 10 to 100 mol %, more preferably 30 to 90 mol %, further preferably 40 to 85 mol % and further more preferably 50 to 80 mol %.

[Hydrocarbon Dispersion Media]

Hydrocarbon dispersion media include, for example, aliphatic hydrocarbons having 6 to 8 carbon atoms such as n-hexane, n-heptane, 2-methylhexane, 3-methylhexane, 2,3-dimethylpentane, 3-ethylpentane, and n-octane; alicyclic hydrocarbons such as cyclohexane, methylcyclohexane, cyclopentane, methylocyclopentane, trans-1,2-dimethylcyclopentane, cis-1,3-dimethylcyclopentane, and trans-1,3-dimethylcyclopentane; and aromatic hydrocarbons such as benzene, toluene, xylene and the like. Among these hydrocarbon dispersion media, in particular, n-hexane, n-heptane, and cyclohexane are suitably used in view of easy industrial availability, stable quality and low cost. These hydrocarbon dispersion media may be used alone or in a combination of two or more. Note that examples of a mixture of hydrocarbon dispersion media include commercially available products such as EXXSOL heptane (made by Exxon Mobil Corporation: containing 75 to 85 mass % of heptane and its isomeric hydrocarbons thereof), which can also produce a suitable result.

For the used amount of the hydrocarbon dispersion medium, it is preferably 100 to 1500 parts by mass relative to 100 parts by mass of a first-step water-soluble ethylenically unsaturated monomer, and more preferably 200 to 1400 parts by mass from the viewpoint that the water-soluble ethylenically unsaturated monomer can be uniformly dispersed to allow easy control over polymerization temperature. Note that as described below, reverse phase suspension polymerization is performed in one step (single step) or in multiple steps such as two or more steps, and the first-step polymerization described above means a polymerization reaction of single-step polymerization or of the first step in multiple-step polymerization (The same shall apply hereinafter).

[Dispersion Stabilizer]
(Surfactant)

In the reverse phase suspension polymerization, in order for dispersion stability in the hydrocarbon dispersion medium of the water-soluble ethylenically unsaturated monomer to be enhanced, a dispersion stabilizer can also be used. A surfactant can be used as the dispersion stabilizer.

As surfactants, the following may be used: for example, sucrose fatty acid ester, polyglycerin fatty acid, sorbitan fatty acid ester, polyoxyethylene sorbitan fatty acid ester, polyoxyethylene glycerine fatty acid ester, sorbitol fatty acid ester, polyoxyethylene sorbitol fatty acid ester, polyoxyethylene alkyl ether, polyoxyethylene alkyl phenyl ether, polyoxyethylene castor oil, polyoxyethylene hydrogenated castor oil, alkyl allyl formaldehyde condensed polyoxyethylene ether, polyoxyethylene polyoxypropylene block copolymer, polyoxyethylene polyoxy propyl alkyl ether, polyethylene glycol fatty acid ester, alkyl glucoside, N-alkyl gluconamide, polyoxyethylene fatty acid amide, polyoxyethylene alkylamine, phosphate ester of polyoxyethylene alkyl ether, phosphate ester of polyoxyethylene alkyl aryl ether and the like. Among these surfactants, in particular, sorbitan fatty acid ester, polyglycerin fatty acid ester, and sucrose fatty acid ester are preferably used in view of dispersion stability of monomers. These surfactants may be used alone or in a combination of two or more.

For the used amount of the surfactant, it is preferably 0.1 to 30 parts by mass relative to 100 parts by mass of a first-step water-soluble ethylenically unsaturated monomer, and more preferably 0.3 to 20 parts by mass.

(Polymeric Dispersion Agent)

A polymeric dispersion agent may also be used, along with a surfactant described above, as a dispersion stabilizer used in the reverse phase suspension polymerization.

Polymeric dispersion agents include, for example, maleic anhydride modified polyethylene, maleic anhydride modified polypropylene, maleic anhydride modified ethylene-propylene copolymer, maleic anhydride modified EPDM (ethylene-propylene-diene-terpolymer), maleic anhydride modified polybutadiene, maleic anhydride-ethylene copolymer, maleic anhydride-propylene copolymer, maleic anhydride-ethylene-propylene copolymer, maleic anhydride-butadiene copolymer, polyethylene, polypropylene, ethylene-propylene copolymer, oxidized polyethylene, oxidized polypropylene, oxidized ethylene-propylene copolymer, ethylene-acrylate copolymer, ethyl cellulose, ethyl hydroxyethyl cellulose and the like. Among these polymeric dispersion agents, particularly in view of dispersion stability of monomers, maleic anhydride modified polyethylene, maleic anhydride modified polypropylene, maleic anhydride modified ethylene-propylene copolymer, maleic anhydride-ethylene copolymer, maleic anhydride-propylene copolymer, maleic anhydride-ethylene-propylene copolymer, polyethylene, polypropylene, ethylene-propylene copolymer, oxidized polyethylene, oxidized polypropylene, and oxidized ethylene-propylene copolymer are preferably used. These polymeric dispersion agents may be used alone or in a combination of two or more.

For the used amount of the polymeric dispersion agents, it is preferably 0.1 to 30 parts by mass relative to 100 parts by mass of a first-step water-soluble ethylenically unsaturated monomer, and more preferably 0.3 to 20 parts by mass.

[Internal-Crosslinking Agent]

Examples of the internal-crosslinking agent include internal-crosslinking agents that can crosslink the polymer of water-soluble ethylenically unsaturated monomers to be used. They include, for example, unsaturated polyesters obtained by reacting a polyol including a diol and a triol such as (poly)ethylene glycol ("(poly)" refers to a case where a prefix "poly" exists and a case where the prefix does not exist. The same shall apply hereinafter.), (poly)propylene glycol, 1,4-butane diol, trimethylolpropane and (poly) glycerin, with an unsaturated acid such as (meth)acrylic acid, maleic acid and fumaric acid; bisacrylamides such as N,N-methylenebisacrylamide; di(meth)acrylic acid esters or tri(meth)acrylic acid esters obtained by allowing polyepoxide to react with (meth)acrylic acid; di(meth)acrylic acid carbamyl esters obtained by allowing polyisocyanate such as tolylene diisocyanate, hexamethylene diisocyanate to react with (meth)acrylic acid hydroxyethyl; compounds having two or more polymerizable unsaturated groups, for example, allylated starch, allylated cellulose, diallyl phthalate, N,N', N"-triallylisocyanate, divinylbenzene and the like; polyglycidyl compounds, for example, diglycidyl compounds such as (poly)ethylene glycol diglycidyl ether, (poly)propylene glycol diglycidyl ether, (poly)glycerin diglycidyl ether, triglycidyl compounds and the like; epihalohydrin compounds such as epichlorohydrin, epibromhydrin, and α-methyl epichlorohydrin; isocyanate compounds such as 2,4-tolylene diisocyanate, and hexamethylene diisocyanate; and compounds having two or more reactive functional groups, for example, oxetane compounds such as 3-methyl-3-oxetane methanol, 3-ethyl-3-oxetane methanol, 3-butyl-3-oxetane methanol, 3-methyl-3-oxetane ethanol, 3-ethyl-3-oxetane ethanol, 3-butyl-3-oxetane ethanol. Among these internal-crosslinking agents, polyglycidyl compounds are preferably used, and diglycidyl ether compounds such as (poly)ethylene glycol diglycidyl ether, (poly)propylene glycol diglycidyl ether, (poly)glycerin diglycidyl ether are particularly preferably used. These internal-crosslinking agents may be used alone or in a combination of two or more.

For the used amount of the internal-crosslinking agent, it is preferably 0.000001 to 0.02 mol relative to 1 mol of a water-soluble ethylenically unsaturated monomer, more preferably 0.00001 to 0.01 mol, further preferably 0.00001 to 0.005 mol and further more preferably 0.00005 to 0.002 mol.

[Azo Based Compound and Peroxide]

In an example of the method of producing a water-absorbent resin, reverse phase suspension polymerization is performed on the water-soluble ethylenically unsaturated monomer in the presence of an azo based compound and a peroxide.

In the above polymerization step, the phrase "in the presence of an azo based compound and a peroxide" does not necessarily means that the azo based compound and the peroxide are coexistent at the beginning of a polymerization reaction, but means that the other compound is present before a monomer conversion ratio by radical cleavage due to one compound becomes 10% or more. However, both are preferably coexistent in an aqueous solution containing a water-soluble ethylenically unsaturated monomer before the start of the polymerization reaction. Further, an azo based compound and a peroxide may be added to a polymerization reaction system via different flow channels or may be sequentially added to the polymerization reaction system via the same flow channel. Note that an azo based compound and a peroxide to be used may be in the form of powder or an aqueous solution.

(Azo Based Compound)

Azo based compounds include, for example, those azo based compounds such as 1-{(1-cyano-1-methylethyl)azo}formamide, 2,2'-azobis[2-(N-phenyl amidino)propane] dihydrochloride, 2,2'-azobis{2-[N-(4-chlorophenyl)amidino]propane}dihydrochloride, 2,2'-azobis{2-[N-(4-hydroxyphenyl)amidino]propane}dihydrochloride, 2,2'-azobis[2-(N-benzyl amidino)propane]dihydrochloride, 2,2'-azobis[2-(N-allyl amidino)propane]dihydrochloride, 2,2'-azobis(2-amidinopropane)dihydrochloride, 2,2'-azobis{2-[N-(2-hydroxyethyl)amidino]propane}dihydrochloride, 2,2'-azobis[2-(5-methyl-2-imidazoline-2-yl)propane]dihydrochloride, 2,2'-azobis[2-(2-imidazoline-2-yl)propane]dihydrochloride, 2,2'-azobis[2-(4,5,6,7-tetrahydro-1H-1,3-diazepine-2-yl)propane]dihydrochloride, 2,2'-azobis[2-(5-hydroxy-3,4,5,6-tetrahydropyrimidine-2-yl)propane] dihydrochloride, 2,2'-azobis{2-[1-(2-hydroxyethyl)-2-imidazoline-2-yl]propane}dihydrochloride, 2,2'-azobis[2-(2-imidazoline-2-yl)propane], 2,2'-azobis{2-methyl-N-[1,1-bis(hydroxymethyl)-2-hydroxyethyl]propionamide}, 2,2'-azobis{2-methyl-N-[1,1-bis (hydroxymethyl)ethyl] propionamide}, 2,2'-azobis[2-methyl-N-(2-hydroxyethyl) propionamide], 2,2'-azobis(2-methylpropionamide) dihydrochloride, 4,4'-azobis-4-cyanovaleinic acid, 2,2'-azobis[2-(hydroxymethyl)propionitrile], 2,2'-azobis[2-(2-imidazoline-2-yl)propane]disulfate dihydrate, 2,2'-azobis [N-(2-carboxyethyl)-2-methylpropione amidine] tetrahydrate, 2,2'-azobis[2-methyl-N-(2-hydroxyethyl) propionamide]. Among these, 2,2'-azobis(2-amidinopropane)dihydrochloride, 2,2'-azobis{2-[1-(2-hydroxyethyl)-2-imidazoline-2-yl] propane}dihydrochloride, 2,2'-azobis[N-(2-carboxyethyl)-2-methylpropione amidine]tetrahydrate are preferred. These compounds may be used alone or in a combination of two or more.

(Peroxide)

Peroxides include, for example, persulfates such as potassium persulfate, ammonium persulfate, and sodium persulfate; peroxides such as methyl ethyl ketone peroxide, methyl isobutyl ketone peroxide, di-t-butyl peroxide, t-butyl cumyl peroxide, t-butyl peroxyacetate, t-butyl peroxy isobutyrate, t-butyl peroxy pivalate, and hydrogen peroxide. Among these peroxides, potassium persulfate, ammonium persulfate, sodium persulfate, and hydrogen peroxide are preferably used, and further, potassium persulfate, ammonium persulfate, and sodium persulfate are more preferably used. These peroxides may be used alone or in a combination of two or more.

(Used Amount and Used Proportion of Azo Based Compound and Peroxide)

For the used amount of an azo based compound and a peroxide, it is preferably 0.00005 mol or more relative to 1 mol of a water soluble ethylenically unsaturated monomer, more preferably 0.0001 mol or more. Further, the used amount is preferably 0.005 mol or less relative to 1 mol of a water-soluble ethylenically unsaturated monomer, and more preferably 0.001 mol or less.

For the used proportion of an azo based compound and a peroxide, the proportion of an azo based compound is preferably 40 mass % or more in the total used amount of an azo based compound and a peroxide, more preferably 50 mass % or more, further preferably 60 mass % or more and further more preferably 70 mass % or more. On the other hand, the proportion of an azo based compound is preferably 95 mass % or less in the total used amount of an azo based compound and a peroxide, more preferably 90 mass % or less, further preferably 85 mass % and further more preferably 80 mass % or less. The mass ratio range (azo based compound:peroxide) is preferably 8:12 to 19:1.

[Other Components]

In an example of the method of producing a water-absorbent resin, other components may be added to an aqueous solution containing a water-soluble ethylenically unsaturated monomer to perform reverse phase suspension polymerization if desired. As other components, various additives such as thickeners and chain transfer agents may be added.

(Thickener)

As an example, a thickener can be added to an aqueous solution containing a water-soluble ethylenically unsaturated monomer to perform reverse phase suspension polymerization. By adding a thickener to adjust the viscosity of an aqueous solution as described above, the median particle diameter obtained by reverse phase suspension polymerization can be controlled.

As a thickener, for example, hydroxyethyl cellulose, hydroxypropyl cellulose, methyl cellulose, carboxymethyl cellulose, polyacrylic acid, (partially) neutralized polyacrylic acid, polyethylene glycol, polyacrylamide, polyethyleneimine, dextrin, sodium alginate, polyvinyl alcohol, polyvinyl pyrrolidone, polyethylene oxide and the like can be used. Note that in a case where the stirring speeds at the time of polymerization are the same, there is a tendency that the higher the viscosity of an aqueous solution of a water-soluble ethylenically unsaturated monomer, the larger the median particle diameter of the resulting particles.

[Reverse Phase Suspension Polymerization]

When performing reverse phase suspension polymerization, a water-soluble ethylenically unsaturated monomer is dispersed in a hydrocarbon dispersion medium in the presence of a surfactant and/or a polymeric dispersion agent. When doing this, a surfactant or a polymeric dispersion agent may be added either before or after the aqueous monomer solution is added as long as they are added before starting a polymerization reaction.

In particular, in view of easy reduction of the amount of a residual hydrocarbon dispersion medium in the resulting water-absorbent resin, it is preferred that polymerization is performed after a water-soluble ethylenically unsaturated monomer is dispersed in a hydrocarbon dispersion medium in which a polymeric dispersion agent has been dispersed, and then a surfactant is further dispersed.

The reverse phase suspension polymerization can be performed as described above in a single step or multiple steps such as two or more steps. Further, in view of increasing productivity, it is preferably performed in 2 to 3 steps.

In a case where reverse phase suspension polymerization is performed in multiple steps such as two or more steps, after a first-step reverse phase suspension polymerization is performed, a water-soluble ethylenically unsaturated monomer may be added to the reaction mixture obtained in the first-step polymerization reaction, and mixed to perform a second-step reverse phase suspension polymerization as in the first step. Preferably, in a case of reverse phase suspension polymerization at each step of the second step and later steps, reverse phase suspension polymerization may be performed by adding, in addition to a water-soluble ethylenically unsaturated monomer, an azo compound and a peroxide described above and an internal crosslinking agent within the aforementioned range of the molar ratio of each component relative to the water-soluble ethylenically unsaturated monomer on the basis of the amount of the water-soluble ethylenically unsaturated monomer to be added in the reverse phase suspension polymerization in each step of the second step and later steps.

For the reaction temperature for a polymerization reaction, it is preferably 20 to 110° C., more preferably 40 to 90° C. from the viewpoint that profitability may be improved by allowing rapid progress of a polymerization to reduce a polymerization time, and polymerization heat may be easily removed to perform a smooth reaction. Further, the reaction time is preferably 0.5 to 4 hours.

Post-Crosslinking Step

Next, in the water-absorbent resin according to the present invention, it is obtained by performing post-crosslinking (post-crosslinking reaction) with a post-crosslinking agent on a hydrous gel-like material obtained by polymerizing a water-soluble ethylenically unsaturated monomer. The post-crosslinking reaction is preferably performed in the presence of the post-crosslinking agent after the polymerization of the water-soluble ethylenically unsaturated monomer. As described above, after the polymerization, the post-crosslinking reaction is performed on the hydrous gel-like material, and thus it is possible to obtain the water-absorbent resin in which the crosslinking density in the vicinity of the surface of the water-absorbent resin is increased, and various performances such as the gel strength and the water-absorption capacity under a load are enhanced.

Post-crosslinking agents can include, but are not limited to, those compounds having two or more reactive functional groups. They include, for example, polyols such as ethylene glycol, propylene glycol, 1,4-butanediol, trimethylolpropane, glycerin, polyoxyethylene glycol, polyoxypropylene glycol, and polyglycerin; polyglycidyl compounds such as (poly)ethylene glycol diglycidyl ether, (poly)glycerin diglycidyl ether, (poly)glycerin triglycidyl ether, trimethylolpropane triglycidyl ether, (poly)propylene glycol polyglycidyl ether, and (poly)glycerol polyglycidyl ether; haloepoxy compounds such as epichlorohydrin, epibromhydrin, and α-methyl epichlorohydrin; isocyanate compounds such as 2,4-tolylene diisocyanate, and hexamethylene diisocyanate; oxetane compounds such as 3-methyl-3-oxetane methanol, 3-ethyl-3-oxetane methanol, 3-butyl-3-oxetane methanol, 3-methyl-oxetane ethanol, 3-ethyl-3-oxetane ethanol, and 3-butyl-3-oxetane ethanol; oxazoline compounds such as 1,2-ethylenebisoxazoline; carbonate compounds such as ethylene carbonate; and hydroxyalkylamide compounds such as bis[N,N-di(β-hydroxyethyl)]adipamide. Among these post-crosslinking agents, particularly preferred are polyglycidyl compounds such as (poly)ethylene glycol diglycidyl ether, (poly)glycerin diglycidyl ether, (poly)glycerin triglycidyl ether, trimethylolpropane triglycidyl ether, (poly)propylene glycol polyglycidyl ether, (poly)glycerol polyglycidyl ether. These post-crosslinking agents may be used alone or in a combination of two or more.

The used amount of a post-crosslinking agent is preferably 0.00001 to 0.01 mol relative to 1 mol of the total amount of a water-soluble ethylenically unsaturated monomer used for polymerization, more preferably 0.00005 to 0.005 mol and particularly preferably 0.0001 to 0.002 mol.

As a method of adding a post-crosslinking agent, the post-crosslinking agent may be added as it is or as an aqueous solution. A post-crosslinking agent may also be added as a solution in which a hydrophilic organic solvent is used as a solvent if desired. Hydrophilic organic solvents include, for example, lower alcohols such as methyl alcohol, ethyl alcohol, n-propyl alcohol, and isopropyl alcohol; ketones such as acetone, and methyl ethyl ketone; ethers such as diethyl ether, dioxane, and tetrahydrofuran; amides such as N,N-dimethylformamide; and sulfoxides such as dimethyl sulfoxide. These hydrophilic organic solvents may be used alone, in a combination of two or more, or in admixture with the water.

As for the timing when a post-crosslinking agent is added, it can be added as long as the polymerization reaction of water-soluble ethylenically unsaturated monomers has been almost completed, but it is preferably added in the presence of water in the range of 1 to 400 parts by mass relative to 100 parts by mass of a water-soluble ethylenically unsaturated monomer, more preferably added in the presence of water in the range of 5 to 200 parts by mass, further preferably added in the presence of water in the range of 10 to 100 parts by mass and further more preferably added in the presence of water in the range of 20 to 60 parts by mass. Note that the amount of water means the total amount of a water content in a polymerization system and a water content used if desired when adding a post-crosslinking agent.

For the reaction temperature in the post-crosslinking reaction, it is preferably 50 to 250° C., more preferably 60 to 180° C., further preferably 60 to 140° C. and further more preferably 70 to 120° C. Further, the reaction time of the post-crosslinking is preferably 1 to 300 minutes, and more preferably 5 to 200 minutes.

Drying Step

A drying step of removing water, a hydrocarbon dispersion medium and the like using distillation by applying energy such as heat from the outside after performing the aforementioned reversed phase suspension polymerization is preferably performed. When performing dehydration of a hydrous gel after reversed phase suspension polymerization, a system in which the hydrous gel is dispersed in a hydrocarbon dispersion medium is heated to temporarily evaporate water and the hydrocarbon dispersion medium from the system by azeotropic distillation. At this time, only the evaporated hydrocarbon dispersion medium is allowed to return into the system, enabling continuous azeotropic distillation. In that case, the temperature in the system during the drying treatment is maintained at or below the azeotropic temperature of the hydrocarbon dispersion medium. Therefore this is preferred from the view point that, for example, the resin is less susceptible to deterioration. Subsequently, water and the hydrocarbon dispersion medium are evaporated away to obtain particles of a water-absorbent resin. By controlling processing conditions of this drying step after polymerization to adjust the amount of dehydrated water, various properties of the resulting water-absorbent resin can be controlled.

In the drying step, the drying treatment may be performed by distillation under ordinary pressure or under reduced pressure. Further, the drying treatment may be performed under a gas flow of nitrogen and the like in view of increased drying efficiency. When performing the drying treatment under ordinary pressure, a drying temperature is preferably 70 to 250° C., more preferably 80 to 180° C., further preferably 80 to 140° C. and particularly preferably 90 to 130° C. Further, when performing the drying treatment under reduced pressure, a drying temperature is preferably 60 to 110° C., more preferably 70 to 100° C.

Note that in a case where post-crosslinking step is performed with a post-crosslinking agent after water-soluble ethylenically unsaturated monomers are polymerized by reversed phase suspension polymerization as described above, the drying step is performed by distillation as described above after the post-crosslinking step. Alternatively, the post-crosslinking step and the drying step may be performed simultaneously.

Further, if desired, various additives such as chelating agents, reducing agents, oxidizing agents, antibacterial agents, and deodorizing agents may be added to a water-absorbent resin after polymerization step and during or after drying step.

3. Absorbent Material and Absorbent Article

The water-absorbent resin according to the present invention forms the absorbent material used for hygienic materials such as sanitary articles and disposable diapers, and is preferably used for an absorbent article including the absorbent material.

Here, an absorbent material in which a water-absorbent resin is used comprises, for example, the water-absorbent resin and a hydrophilic fiber. The structures of the absorbent material include a dispersion mixture obtained by mixing a water-absorbent resin and a hydrophilic fiber to give a uniform composition, a sandwich structure in which a water-absorbent resin is sandwiched between layered hydrophilic fibers, a structure in which a water-absorbent resin and a hydrophilic fiber are wrapped in tissue, and the like. Note that other components, for example, an adhesive binder such as thermal adhesive synthetic fibers, hot melt adhesives, and adhesive emulsions for increasing the shape retention capability of an absorbent material may be included in the absorbent material.

For the content of a water-absorbent resin in an absorbent material, it is preferably 5 to 95 mass %, more preferably 20 to 90 mass % and further preferably 30 to 80 mass %. When the content of a water-absorbent resin is less than 5 mass %, the absorption capacity of an absorbent material may be decreased, resulting in leakage and re-wet of a liquid. On the other hand, when the content of a water-absorbent resin is more than 95 mass %, the cost of an absorbent material increases, and the touch of the absorbent material becomes harder.

Hydrophilic fibers include cellulose fibers such as cotton-like pulp obtained from wood, mechanical pulp, chemical pulp, and semichemical pulp; artificial cellulose fibers such as rayon, and acetate; and fibers comprising synthetic resin such as hydrophilized polyamide, polyester, and polyolefins.

Moreover, an absorbent material in which a water-absorbent resin is used can be held between a liquid permeable sheet (top sheet) through which a liquid can permeate and a liquid impermeable sheet (back sheet) through which a liquid cannot permeate to give an absorbent article. The liquid permeable sheet is arranged on the side to be in contact with the body while the liquid impermeable sheet is arranged opposite to the side to be in contact with the body.

Liquid permeable sheets include non-woven and porous synthetic resin sheets of an air through type, a span bond type, a chemical bond type, a needle punch type and the like comprising fiber such as polyethylene, polypropylene, polyester and the like. Further, liquid impermeable sheets include synthetic resin films comprising a resin such as polyethylene, polypropylene, polyvinyl chloride and the like.

EXAMPLES

4. Example

Hereafter, the present invention will be described in more detail with reference to Examples and Comparative Examples. However, the present invention shall not in any way be limited to the following Examples and the like.

4-1. Method for Evaluation Test

Water-absorbent resins obtained from Examples, and Comparative Examples below were subjected to various tests described below for evaluation. In the following, each evaluation test method will be described.

(1) Yellow Index 2.0 g of a water-absorbent resin was put into a glass measurement container having an inside diameter of 3 cm, and the yellow index of the water-absorbent resin was measured with a color-difference meter (Color Meter ZE2000 made by Nippon Denshoku Industries Co. Ltd.) in which the tristimulus values, X, Y and Z of a colorimetric color-difference meter are corrected with a standard white plate, and the yellow index was calculated by the formula below from the obtained X, Y and Z (tristimulus values) of the water-absorbent resin.

$$\text{yellow index} = 100\ (1.28X - 1.06Z)/Y$$

(Gel Strength)

49.0 g of 0.9 mass % sodium chloride aqueous solution (physiological saline) was measured and put into a 100 mL beaker, and a magnetic stirrer bar (8 mm $\phi \times 30$ mm without a ring) was put thereinto and was arranged on a magnetic stirrer (made by Iuchi Co., Ltd.: HS-30D). Then, the magnetic stirrer bar was adjusted so as to be rotated at 600 revolutions per minute.

Then, 1.0 g of the water-absorbent resin was put into a beaker under stirring, was continued to be stirred until rotating vortexes disappeared and the liquid surface was brought into a horizontal position, thereby adjusting the gel. The gel was stored in a constant temperature and humidity chamber under conditions of 40° C. and 60% RH for 15 hours, and was used as a measurement sample.

The gel elastic modulus of the measurement sample was measured with a card meter (made by I. Techno Engineering Co., Ltd.: Card Meter Mini ME-600). The measuring conditions of the card meter were as follows.

Pressure-sensing shaft: 16 mm $\phi$
Spring: for 400 g
Load: 400 g
Rate of rise: 1 inch/21 sec
Test mode: Viscous (3) Water-Absorption Capacity of Physiological Saline Under a Load of 4.14 kPa A water-absorption capacity of physiological saline under a load of 4.14 kPa of a water-absorbent resin was measured using a measurement apparatus X. A schematic arrangement of the measurement apparatus X is shown in FIG. 1.

The measurement apparatus X shown in FIG. 1 comprises a buret part 1, a conduit 2, a measurement stage 3, and a measurement part 4 placed on the measurement stage 3. In the buret part 1, a rubber stopper 14 is connected to the upper part of a buret 10, and an air introducing pipe 11 and a cock 12 is connected to the lower part of the buret 10. Further, a cock 13 is attached to the upper part of the air introducing pipe 11. A conduit 2 connects the buret part 1 and the measurement stage 3. The diameter of the conduit 2 is 6 mm. The measurement stage 3 has a hole with a diameter of 2 mm at the center, to which the conduit 2 is connected. The measurement part 4 is provided with a cylinder 40 and a nylon mesh 41 patched on the bottom of the cylinder 40, as well as a weight 42. The inner diameter of the cylinder 40 is 2.0 cm. The nylon mesh 41 is formed as 200 mesh (75 μm openings). Further, it is configured such that a predetermined amount of a water-absorbent resin 5 is uniformly distributed on the nylon mesh 41. The weight 42 has a diameter of 1.9 cm and a mass of 119.6 g. The weight 42 is to be placed on the water-absorbent resin 5 to uniformly apply a load of 4.14 kPa to the water-absorbent resin 5.

Using the measurement apparatus X having a structure as described above, first, the cock 12 and the cock 13 at the buret part 1 were closed, and then physiological saline adjusted to 25° C. was introduced into the buret 10 from the top. Subsequently, the top of the buret was plugged with the rubber stopper 14, and then the cock 12 and the cock 13 at the buret part 1 were opened. Next, the height of the measurement stage 3 was adjusted so that the tip of the conduit 2 at the center of the measurement stage 3 was leveled with the air inlet of the air introducing pipe 11.

Meanwhile, 0.10 g of the water-absorbent resin 5 was uniformly distributed on the nylon mesh 41 in the cylinder 40, and then the weight 42 was placed on that water-absorbent resin 5. The measurement part 4 was arranged so that its center coincided with the conduit inlet at the center of the measurement stage 3.

The amount of reduced physiological saline in the buret 10 (the amount of physiological saline absorbed by the water-absorbent resin 5) Wa (mL) was continuously measured from the time point when the water-absorbent resin 5 started to absorb water. At an elapsed time of 60 minutes from the start of water absorption, a water-absorption capacity of physiological saline under a load of 4.14 kPa of the water-absorbent resin was calculated by the following formula.

Water-absorption capacity of physiological saline under a load of 4.14 kPa (mL/g)=$Wa$/0.10 (g)

(4) Median Particle Diameter (Particle Size Distribution)

To 50 g of a water-absorbent resin, 0.25 g of amorphous silica (made by Evonik Degussa Japan, Inc., Carplex #80) was mixed as a lubricant.

JIS standard sieves were combined in the following order from the top: a sieve of 850 μm openings, a sieve of 600 μm openings, a sieve of 500 μm openings, a sieve of 400 μm openings, a sieve of 300 μm openings, a sieve of 250 μm openings, a sieve 150 μm openings and a receiving tray.

The water-absorbent resin was introduced into the top of the combined sieves, and then shaken for 20 minutes using a ro-tap shaker for classification. After classification, the mass of the water-absorbent resin which remained in each sieve was calculated as a mass percentage relative to the total mass to obtain a particle size distribution. By integrating the amount on each sieve from the one having the largest particle diameter in this particle size distribution, the relationship between the sieve openings and the integrated value of the mass percentage of the water-absorbent resin which remained in the sieves was plotted on logarithmic probability paper. By connecting the plots on the probability paper with a straight line, a particle diameter corresponding to 50 mass % in the integrated mass percentage was taken as the median particle diameter.

Note that the mass proportion of particles from 300 to 400 μm in the total water-absorbent resin is a mass proportion of a water-absorbent resin which remained in the sieve with 300 μm openings relative to the whole in the aforementioned measurements. Similarly, the mass proportion of particles from 150 to 850 μm in the total water-absorbent resin is a value obtained by summing the mass proportion of the water-absorbent resin which remained in sieves with openings of 150 μm, 250 μm, 300 μm, 400 μm, 500 μm, and 600 μm.

(5) Flowability After Moisture Absorption Test 0.03 g of amorphous silica (made by Evonik Degussa Japan, Inc., Carplex #80) was mixed as a lubricant with 10 g of the water-absorbent resin.

The mixture was uniformly put into a stainless petri dish having a diameter of 10 cm, and was left still for 1 hour in a constant temperature and humidity chamber maintained at 40° C. and a relative humidity of 90% RH. The mass (Wb) of the sample that absorbed moisture after one-hour of still placement was measured.

The sample after the moisture absorption was carefully transferred to a 12-meshed sieve (JIS standard sieve) where a receiving tray was placed, and the sieve was lightly tapped five times with the palm of a hand. Then, the sieve was rotated in a circumferential direction by 90 degrees, and thereafter was further lightly tapped five times. The mass (Wc) of the sample after the moisture absorption that passed through the 12-meshed sieve and was left on the receiving tray was measured, and the flowability (%) after the moisture absorption test was determined by the formula below.

flowability (%) after the moisture absorption test=$Wc/Wb$×100

[Evaluation Test of Absorbent Material in which Water-Absorbent Resin is Used]
(1) Production of Absorbent Material With an airflow-type mixing device (made by O-TEC Co., Ltd., Pad Former), 80 mass parts of the water-absorbent resin and 20 mass parts of crushed pulp (made by Rayonier, Rayfloc) were mixed, and the mixture was distributed such that its basis weight was about 500 g/m². The obtained product was cut into a sheet of 40 cm×12 cm, and thus an absorbent material core was produced. Next, absorbent material A was prepared by pressing the absorbent material core with a load of 196 kPa applied to the whole for 30 seconds, the absorbent material core being sandwiched by two sheets of tissue paper having a basis weight of 16 g/m² and the same size as the absorbent material core.

Absorbent material B was prepared in the same method as described above except that 80 mass parts of the water-absorbent resin that was left still for 1 hour in a constant temperature and humidity chamber maintained at 40° C. and a relative humidity of 90% RH and 20 mass parts of crushed pulp (made by Rayonier, Rayfloc) were used.

Appearance Evaluation of Absorbent Material

The appearance of absorbent material A was evaluated with the following method. Specifically, 10 panelists were selected, the appearance (cleanliness) of the obtained absorbent material was evaluated with the following criteria in three stages, the evaluation values of the panelists were averaged and thus the appearance of the absorbent material was evaluated.

Stage A: white and clean (evaluation value: 5)
Stage B: slightly yellowish (evaluation value: 3)
Stage C: yellowish (evaluation value: 1)

Workability at the Time of Manufacturing Absorbent Material

According to the manufacturing process described in the manufacturing example described above, absorbent material B was manufactured successively 10 times in a row.

The states of the water-absorbent resin, absorbent material B and the absorbent manufacturing machine after the manufacturing were evaluated by three workers with criteria shown in table 1 below in three stages, the evaluation values of each item were averaged and thus the workability at the time of manufacturing of the absorbent material was evaluated.

TABLE 1

| Evaluation items | Criteria | Evaluation values |
| --- | --- | --- |
| State of distribution of mixture | State of distribution is uniform, and reproducibility is high | 5 |
| | State of distribution is sometimes unbalanced and non-uniform | 3 |
| | State of distribution is often unbalanced and non-uniform | 1 |
| Adherence of powder to manufacturing machine | Adherence to manufacturing machine is hardly recognized | 5 |
| | A small amount is adhered but can be removed by air injection | 3 |
| | A large amount is adhered and needs to be removed with hard brush | 1 |

4-2. Examples and Comparative Example

Example 1

A 2 cylindrical round-bottom separable flask with an inner diameter of 110 mm was prepared and equipped with a reflux condenser, a dropping funnel, a nitrogen gas-introducing tube and stirrer having stirring blades compound of two sets of 4 inclined paddle blades with a blade diameter of 50 mm. To this flask, 300 g of n-heptane was introduced as a hydrocarbon dispersion medium, 0.74 g of sucrose stearic acid ester of HLB3 (made by Mitsubishi-Kagaku Foods Corporation, RYOTO sugar ester S-370) was added as a surfactant and 0.74 g of maleic anhydride modified ethylene-propylene copolymer (made by Mitsui Chemicals, Inc., High Wax 1105A) was added as a polymeric dispersion agent, and heated to 80° C. with stirring, and a surfactant was dissolved, and then cooled to 50° C.

Meanwhile, 92 g (1.02 mol) of 80 mass % aqueous acrylic acid was introduced into a 500 mL Erlenmeyer flask, and 102.2 g of 30 mass % aqueous sodium hydroxide was added dropwise while cooling from the outside to perform 75 mol % neutralization. Subsequently, 0.092 g of hydroxylethyl cellulose (made by Sumitomo Seika Chemicals Co., Ltd., HEC AW-15F) as a thickener, 0.092 g (0.339 mmol) of 2,2'-azobis(2-amidinopropane)dihydrochloride as an azo based compound, 0.037 g (0.137 mmol) of potassium persulfate as a peroxide, 0.020 g (0.116 mmol) of ethylene glycol diglycidyl ether as an internal-crosslinking agent and 43.8 g of ion exchange water were added and dissolved to prepare a first-step aqueous monomer solution.

Then the aqueous monomer solution prepared as described above was added to a separable flask, and the atmosphere in the system was thoroughly replaced with nitrogen. Then, the flask was immersed into a 70° C. water bath to raise temperature, and polymerization was performed for 60 minutes to obtain a first-step polymerized slurry.

Meanwhile, 128.8 g (1.43 mol) of 80 mass % aqueous acrylic acid was introduced to another 500 mL Erlenmeyer flask, and 143.1 g of 30 mass % aqueous sodium hydroxide was added dropwise while cooling from the outside to perform 75 mol % neutralization. Subsequently, 0.129 g (0.475 mmol) of 2,2'-azobis(2-amidinopropane)dihydrochloride as an azo based compound, 0.052 g (0.191 mmol) of potassium persulfate as a peroxide, 0.012 g (0.067 mmol) of ethylene glycol diglycidyl ether as an internal-crosslinking agent and 15.9 g of ion exchange water were added and dissolved to prepare a second-step aqueous monomer solution.

After cooling the system in the aforementioned separable flask to 25° C., all of the second-step aqueous monomer solution was added to the first-step polymerized slurry, and the atmosphere in the system was thoroughly replaced with nitrogen. Subsequently, the flask was again immersed into a 70° C. water bath to raise temperature, and a second-step polymerization was performed for 30 minutes.

After the second-step polymerization, the reaction liquid was heated to 125° C. in an oil bath, and 252 g of water was removed from the system by refluxing n-heptane in azeotropic distillation of n-heptane and water. Then, 4.42 g (0.51 mmol) of 2 mass % aqueous solution of ethylene glycol diglycidyl ether was added as a post-crosslinking agent, and maintained at 80° C. for 2 hours. Subsequently drying step was performed by evaporating n-heptane, and then a dried resin was obtained. The dried resin was allowed to pass through a sieve with 1000 μm openings to obtain 231.2 g of a water-absorbent resin in a form of agglomerated spherical particles. The water-absorbent resin obtained in this way was evaluated in accordance with the various test methods as described above.

Note that for the water-absorbent resin obtained, the mass proportion of particles from 150 to 850 μm relative to the whole proportion was 95 mass %, the mass proportion of particles from 300 to 400 μm was 33 mass % and the median particle diameter was 370 μm.

Example 2

In Example 2, the same was performed as in Example 1 except that after the second-step polymerization, 255 g of water was removed from the system by refluxing n-heptane in azeotropic distillation of n-heptane and water. Thereby, 232.1 g of a water-absorbent resin was obtained having a different water-absorption capacity from the water-absorbent resin obtained in Example 1. The water-absorbent resin obtained in this way was evaluated in accordance with the various test methods as described above.

Note that for the water-absorbent resin obtained, the mass proportion of particles from 150 to 850 μm relative to the whole proportion was 95 mass %, the mass proportion of particles from 300 to 400 μm was 33 mass % and the median particle diameter was 375 μm.

Example 3

Example 3 was the same as Example 1 except that a peroxide dissolved in a first-step monomer aqueous solution was 0.033 g (0.137 mmol) of sodium persulfate, and that a peroxide dissolved in a second-step monomer aqueous solution was 0.045 g (0.189 mmol) of sodium persulfate. Thereby, 231.8 g of a water-absorbent resin that differs from the water-absorbent resin obtained in Example 3 in the type of peroxide used in the polymerization was obtained. The water-absorbent resin thus obtained was evaluated according to the various types of test methods described above.

Note that for the water-absorbent resin obtained, the mass proportion of particles from 150 to 850 μm relative to the whole proportion was 94 mass %, the mass proportion of particles from 300 to 400 μm was 33 mass % and the median particle diameter was 360 μm.

Comparative Example 1

In Comparative Example 1, a 2 cylindrical round-bottom separable flask with an inner diameter of 110 mm was prepared and equipped with a reflux condenser, a dropping funnel, a nitrogen gas-introducing tube and stirrer having stirring blades compound of two sets of 4 inclined paddle blades with a blade diameter of 50 mm. To this flask, 300 g of n-heptane was introduced as a hydrocarbon dispersion medium, 0.74 g of sucrose stearic acid ester of HLB3 (made by Mitsubishi-Kagaku Foods Corporation, Ryoto sugar ester S-370) was added as a surfactant and 0.74 g of maleic anhydride modified ethylene-propylene copolymer (made by Mitsui Chemicals, Inc., High Wax 1105A) was added as a polymeric dispersion agent, and heated to 80° C. with stirring, and a surfactant was dissolved, and then cooled to 50° C.

Meanwhile, 92 g (1.02 mol) of 80 mass % aqueous acrylic acid was introduced into a 500 mL Erlenmeyer flask, and 102.2 g of 30 mass % aqueous sodium hydroxide was added dropwise while cooling from the outside to perform 75 mol % neutralization. Subsequently, 0.092 g of hydroxyethyl cellulose (made by Sumitomo Seika Chemicals Co., Ltd., HEC AW-15F) as a thickener, 0.074 g (0.274 mmol) of potassium persulfate as a peroxide, 0.010 g (0.058 mmol) of ethylene glycol diglycidyl ether as an internal-crosslinking agent and 43.8 g of ion exchange water were added and dissolved to prepare a first-step aqueous monomer solution.

Then, the aqueous monomer solution prepared as described above was added to a separable flask, and the atmosphere in the system was thoroughly replaced with nitrogen. Then, the flask was immersed into a 70° C. water bath to raise temperature, and polymerization was performed for 60 minutes to obtain a first-step polymerized slurry.

Meanwhile, 128.8 g (1.43 mol) of 80 mass % aqueous acrylic acid was introduced to another 500 mL Erlenmeyer flask, and 143.1 g of 30 mass % aqueous sodium hydroxide was added dropwise while cooling from the outside to perform 75 mol % neutralization. Then, 0.104 g (0.382 mmol) of potassium persulfate as a peroxide, 0.012 g (0.067 mmol) of ethylene glycol diglycidyl ether as an internal-crosslinking agent and 15.9 g of ion exchange water were added and dissolved to prepare a second-step aqueous monomer solution.

After cooling the system in the aforementioned separable flask to 25° C., all of the second-step aqueous monomer solution was added to the first-step polymerized slurry, and the atmosphere in the system was thoroughly replaced with nitrogen. Subsequently, the flask was again immersed into a 70° C. water bath to raise temperature, and a second-step polymerization was performed for 30 minutes.

After the second-step polymerization, the reaction liquid was heated to 125° C. in an oil bath, and 257 g of water was removed from the system by refluxing n-heptane in azeotropic distillation of n-heptane and water. Then, 4.42 g (0.51 mmol) of 2 mass % aqueous solution of ethylene glycol diglycidyl ether was added as a post-crosslinking agent, and maintained at 80° C. for 2 hours. Subsequently, drying step was performed by evaporating n-heptane to obtain a dried resin. The dried resin was allowed to pass through a sieve with 1000 μm openings to obtain 228.2 g of a water-absorbent resin in a form of agglomerated spherical particles. The water-absorbent resin obtained in this way was evaluated in accordance with the various test methods as described above.

Note that for the obtained water-absorbent resin, the mass proportion of particles from 150 to 850 μm relative to the whole proportion was 95 mass %, the mass proportion of particles from 300 to 400 μm was 31 mass % and the median particle diameter was 350 μm.

Comparative Example 2

In Comparative Example 2, the same was performed as in Comparative Example 1 except that the addition amount of ethylene glycol diglycidyl ether as an internal-crosslinking agent to be dissolved in the first-step aqueous monomer solution was 0.016 g (0.090 mmol), the addition amount of ethylene glycol diglycidyl ether as an internal-crosslinking agent to be dissolved in the second-step aqueous monomer solution was 0.014 g (0.074 mmol) and after the second-step polymerization, 257 g of water was removed from the system by refluxing n-heptane in azeotropic distillation of n-heptane and water, and 6.64 g (0.77 mmol) of 2 mass % aqueous solution of ethylene glycol diglycidyl ether was added. 230.4 g of a water-absorbent resin was obtained. The water-absorbent resin obtained in this way was evaluated in accordance with the various test methods as described above.

Note that for the water-absorbent resin obtained, the mass proportion of particles from 150 to 850 μm relative to the whole proportion was 95 mass %, the mass proportion of particles from 300 to 400 μm was 33 mass % and the median particle diameter was 375 μm.

Comparative Example 3

In Comparative Example 3, the same was performed as in Comparative Example 1 except that the addition amount of ethylene glycol diglycidyl ether as an internal-crosslinking agent to be dissolved in the first-step aqueous monomer solution was 0.011 g (0.063 mmol), the addition amount of ethylene glycol diglycidyl ether as an internal-crosslinking agent to be dissolved in the second-step aqueous monomer solution was 0.014 g (0.074 mmol) and after the second-step polymerization, 263 g of water was removed from the system by refluxing n-heptane in azeotropic distillation of n-heptane and water, and 3.32 g (0.39 mmol) of 2 mass % aqueous solution of ethylene glycol diglycidyl ether was added as a post-crosslinking agent. 229.6 g of a water-absorbent resin was obtained. The water-absorbent resin obtained in this way was evaluated in accordance with the various test methods as described above.

Note that for the water-absorbent resin obtained, the mass proportion of particles from 150 to 850 μm relative to the whole proportion was 92 mass %, the mass proportion of particles from 300 to 400 μm was 30 mass % and the median particle diameter was 360 μm.

4-3. Evaluation Results

[Evaluation of Water-Absorbent Resin]

The evaluation results of the water-absorbent resins obtained in Examples 1 to 3 and Comparative Examples 1 to 3 are shown in table 2 below.

TABLE 2

| | Water-absorption capacity (g/g) | Yellow index (—) | Gel strength (Pa) | Flowability after moisture absorption test (%) | Water-absorption capacity of physiological saline under a load of 4.14 kPa (ml/g) |
|---|---|---|---|---|---|
| Example 1 | 60 | 4.6 | 1230 | 80 | 22 |
| Example 2 | 67 | 4.8 | 1450 | 70 | 18 |
| Example 3 | 59 | 4.6 | 960 | 61 | 23 |
| Comparative Example 1 | 61 | 10.4 | 1570 | 44 | 15 |
| Comparative Example 2 | 55 | 10.1 | 1920 | 48 | 25 |
| Comparative Example 3 | 68 | 10.5 | 750 | 27 | 9 |

As shown in table 2, the water-absorbent resins obtained in the examples where the yellow index and the gel strength fell within predetermined numerical ranges were excellent in the flowability after the moisture absorption test as compared with the water-absorbent resins in the comparative examples.

[Evaluation of Absorbent Material and Workability Evaluation at the Time of Manufacturing Absorbent Material]

The results of the evaluation of the absorbent materials manufactured with the water-absorbent resins obtained in examples 1 to 3 and comparative examples 1 to 3 and the workability evaluation at the time of manufacturing of the absorbent materials are shown in table 3 below.

TABLE 3

| | Absorbent material evaluation results | |
|---|---|---|
| | Appearance | Workability at the time of manufacturing |
| Example 1 | 4.4 | 4.3 |
| Example 2 | 4.4 | 4.0 |
| Example 3 | 4.2 | 4.0 |
| Comparative Example 1 | 3.0 | 2.3 |
| Comparative Example 2 | 3.2 | 2.0 |
| Comparative Example 3 | 2.6 | 1.3 |

As shown in table 3, the absorbent materials in which the water-absorbent resins of the examples were used were excellent in the appearance (cleanliness), furthermore were excellent in the workability at the time of manufacturing in the manufacturing process of the absorbent materials and were excellent in the dispersion of the water-absorbent resins as compared with the case where the water-absorbent resins of the comparative examples were used.

EXPLANATION OF REFERENCE NUMERALS

X measurement apparatus
1 buret part
2 conduit
3 measurement stage
4 measurement part
5 water-absorbent resin

The invention claimed is:

1. A water-absorbent resin,
the water-absorbent resin being obtained by polymerizing a water-soluble ethylenically unsaturated monomer by using an aqueous solution polymerization method, an emulsion polymerization method, or a reverse phase suspension polymerization method, in the presence of an internal-crosslinking agent and in the presence of an azo based compound and a persulfate, and performing post-crosslinking thereon with a post-crosslinking agent,
a monomer of 70 to 100 mol% in the water-soluble ethylenically unsaturated monomer being acrylic acid or salt thereof, and
the water-absorbent resin satisfies the requirements below:
(A) yellow index is 5.0 or less;
(B) gel strength is 500 Pa or more and 1800 Pa or less; and
(C) a water-absorption capacity of physiological saline under a load of 4.14 kPa is 16 ml/g or more.

2. An absorbent article that uses an absorbent material comprising the water-absorbent resin according to claim 1.

3. The water-absorbent resin according to claim 1, wherein a mass ratio of the azo based compound to the persulfate is 8:12 to 19:1.

* * * * *